US012582734B2

(12) United States Patent
Bermudez Guerrero et al.

(10) Patent No.: US 12,582,734 B2
(45) Date of Patent: Mar. 24, 2026

(54) SYSTEM FOR PREVENTING SCALING, REMOVING HYDROGEN PEROXIDE RESIDUES AND RECYCLING WATER IN A SEPTIC FILLING SYSTEMS OF LAMINATED CARTON CONTAINERS

(71) Applicants: Gustavo Bermudez Guerrero, Tlalnepantla de Baz (MX); Sergio Michel Brambila, Tlalnepantla de Baz (MX); Guillermo Vazquez De Anda, Tlalnepantla de Baz (MX)

(72) Inventors: Gustavo Bermudez Guerrero, Tlalnepantla de Baz (MX); Sergio Michel Brambila, Tlalnepantla de Baz (MX); Guillermo Vazquez De Anda, Tlalnepantla de Baz (MX)

( * ) Notice: Subject to any disclaimer, the term of this patent is extended or adjusted under 35 U.S.C. 154(b) by 758 days.

(21) Appl. No.: 17/312,271

(22) PCT Filed: Nov. 21, 2019

(86) PCT No.: PCT/IB2019/060052
§ 371 (c)(1),
(2) Date: Jun. 9, 2021

(87) PCT Pub. No.: WO2020/121089
PCT Pub. Date: Jun. 18, 2020

(65) Prior Publication Data

US 2022/0031888 A1 Feb. 3, 2022

(30) Foreign Application Priority Data

Dec. 10, 2018 (MX) ....................... MX/2018/015316

(51) Int. Cl.
*B65B 55/02* (2006.01)
*A61L 2/186* (2026.01)
(Continued)

(52) U.S. Cl.
CPC ................. *A61L 2/186* (2013.01); *A61L 2/26* (2013.01); *B01D 53/1493* (2013.01);
(Continued)

(58) Field of Classification Search
CPC ......... B65B 31/02; B65B 55/10; B65B 55/04; A61L 2/186; A61L 2/26; C02F 1/722
(Continued)

(56) References Cited

U.S. PATENT DOCUMENTS 3,884,012 A * 5/1975 Ernstsson ............. B65B 55/103
53/511
4,971,714 A * 11/1990 Lokkesmoe ....... C11D 17/0017
510/225

(Continued)

FOREIGN PATENT DOCUMENTS

| | | | |
|---|---|---|---|
| EP | 0597356 | A2 | 5/1994 |
| FR | 2195550 | A1 | 3/1974 |
| WO | 2009/095182 | A2 | 1/2009 |

OTHER PUBLICATIONS

International Search Report (ISR) and Written Opinion (WO) issued Feb. 28, 2020 in corresponding PCT Application No. PCT/IB2019/060052, includes English translation of ISR, 16 pages.

*Primary Examiner* — Monzer R Chorbaji
(74) *Attorney, Agent, or Firm* — MH2 Technology Law Group LLP

(57) ABSTRACT

Disclosed is a system for preventing scaling and deposit formation in a sterile air heat exchanger of a system for aseptic packaging within laminated carton packages, and a process for eliminating hydrogen peroxide residues in aseptic laminated carton packaging systems, characterized in that it comprises providing a supply of water for scrubbing
(Continued)

sterile air that has the following properties: (a) maximum conductivity at 20° C. of 2.0 micromhos; and (b) a maximum silica content of 0.1 ppm.

8 Claims, 7 Drawing Sheets

(51) Int. Cl.

| | |
|---|---|
| ***A61L 2/26*** | (2006.01) |
| ***B01D 53/14*** | (2006.01) |
| ***B65B 55/10*** | (2006.01) |
| ***C02F 1/00*** | (2023.01) |
| ***C02F 1/32*** | (2023.01) |
| ***C02F 1/72*** | (2023.01) |
| ***F26B 3/00*** | (2006.01) |
| *A61L 101/02* | (2006.01) |
| *A61L 103/00* | (2026.01) |
| *C02F 101/10* | (2006.01) |
| *C02F 103/34* | (2006.01) |

(52) U.S. Cl.
CPC .............. *B65B 55/10* (2013.01); *C02F 1/001* (2013.01); *C02F 1/32* (2013.01); *C02F 1/722* (2013.01); *A61L 2101/02* (2020.08); *A61L 2103/23* (2026.01); *A61L 2202/17* (2013.01); *B01D 2252/103* (2013.01); *C02F 2101/10* (2013.01); *C02F 2103/34* (2013.01); *C02F 2303/04* (2013.01)

(58) Field of Classification Search
USPC ...................................... 53/180, 425; 34/357
See application file for complete search history.

(56) References Cited

U.S. PATENT DOCUMENTS

| | | | | |
|---|---|---|---|---|
| 5,407,583 | A * | 4/1995 | Gill | C02F 5/14<br>210/698 |
| 6,183,691 | B1 | 2/2001 | Swank et al. | |
| 9,850,154 | B2 * | 12/2017 | Musale | C02F 9/00 |
| 2009/0203516 | A1 * | 8/2009 | Kirkpatrick | B08B 9/20<br>502/22 |
| 2011/0016829 | A1 | 1/2011 | Drenguis et al. | |
| 2013/0252869 | A1 * | 9/2013 | Oh | C11D 1/835<br>510/491 |
| 2014/0121146 | A1 * | 5/2014 | Miralles | C11D 7/265<br>510/513 |

* cited by examiner

SYSTEM FOR PREVENTING SCALING, REMOVING HYDROGEN PEROXIDE RESIDUES AND RECYCLING WATER IN A SEPTIC FILLING SYSTEMS OF LAMINATED CARTON CONTAINERS

CROSS REFERENCE TO RELATED APPLICATIONS

This patent application is a national stage entry from International Application No. PCT/IB2019/060052, filed on Nov. 21, 2019, published as International Publication No. WO 2020/121089 A1 on Jun. 18, 2020, and claims priority under 35 U.S.C. § 119 from Mexican patent application MX2018015316A, filed Dec. 10, 2018, the entire contents of all of which are incorporated by reference herein.

FIELD OF THE INVENTION

This invention relates to the field of sanitization systems for packages that contain laminated carton, it has the aim of preventing the formation of scale and deposits that take place in the sterile air heat exchangers of said sanitation systems, which cause stoppages for its cleaning and production losses, in addition specifically, this invention provides the elimination of Hydrogen Peroxide residues and a reduction in the recirculation water used (utilities) in the air washing, in aseptic packaging in machines that fill laminated carton packages.

BACKGROUND OF THE INVENTION

Over time, packaging techniques have been developed, providing container in which it is possible to offer hygienically fresh products, for this reason machinery has been developed for the packaging and conservation of products, along with, a diversity of materials have been developed, as well as different types of product preservation treatments, within a wide market in food preservation techniques.

For the packaging of these food products, have been developed the laminated carton packages, which are commonly used to package dairy products, pasteurized and ultra-pasteurized juices. Such products are commonly packaged in laminated carton packages that are preformed, with a bottom closed before being filled under a sterile control, it is to say, aseptic conditions of packaging.

The packaging of the food product in said laminated carton packages, requires sanitization of the container before being filled, in order to substantially reduce the microbial content, up to a safe desired level.

Said sanitization process of laminated carton containers is commonly carried out using specialized machines, in which, before the container is formed, the laminated carton sheet is passed through a step of hydrogen peroxide bath to eliminate the bacteria that cause degradation of the product to be contained. Then, a drying step is carried out, and finally there is an step of formation of the package and subsequently a food product is packaged within the laminated carton container, and the container is closed.

According to the common technique, Hydrogen peroxide residues must be removed by applying hot air prior to packaging forming and product filling.

The known systems to achieve the sanitization of the laminated carton packages require water that is subsequently poured into the drain. Although it is a question of separating such valuable compound from the water, the techniques of the prior art have not considered to recover and recycle the wastewater containing hydrogen peroxide to the process. Therefore, according to the present invention, it is provided a loop that contains a chiller or water cooler, a filtration system using activated carbon, green sand or a combination of both and an ultraviolet light lamp, which allows the water used to wash the sterile air to be reused, thereby preventing the salts from precipitating and form scale within the sterile air heat exchanger, as well as eliminating the residual hydrogen peroxide in the machines aseptic packaging, thus helping to reduce the consumption of fresh water required for the operation, as well as increasing the productivity by keeping the sterile air heat exchanger clean.

At present, there are some systems of which the following can be mentioned:

Great Britain Patent Application GB 1394917 dated May 1, 1975, by Tetra Pak International AB titled Aseptic Packaging of Materials, in which it is disclosed an aseptic packaging method, in said patent application a sterilization process is carried out on a thermoformable material, which is submerged in liquid chambers containing hydrogen peroxide and then the remnant solution is dried by heat or by air, the volatility of the remnant that is impregnated to the material of the aseptic solution is high and there is no recovery thereof by any known method, In contrast, the present invention a provides a closed loop system.

U.S. Pat. No. 3,282,702, the technique to remove hydrogen peroxide residues, disclosed in said patent consists of the use of an immobilized enzyme. The enzyme used is a catalase. It has as a drawback, the risk of introducing organic matter due to the enzyme and the process is expensive.

U.S. Pat. No. 4,551,553 discloses an hydroperoxide decomposition process using a catalyst consisting of a salt of chromium and ruthenium, however, these are heavy metals which in turn are concentrated and introduced into the aseptic system.

U.S. Pat. No. 4,873,380, uses a catalyst that contains oxides of nickel, copper, chromium and barium to decompose hydro peroxides contained in tertiary butyl and butyl peroxides contained in tertiary butyl alcohol, however, these are heavy metals which in turn become concentrated and introduced into the aseptic system.

Mexican Patent Application No. MX/a/2016/000161, called the Aseptic Packaging Machine Water Recovery System, of the applicant Comercializadora de Lácteos y Derivados, S.A. de C.V. and the Instituto Tecnológico Superior de Lerdo, uses iron salts and hydrogen peroxide added in a reactor to carry out the reaction (known as the Fenton reaction) for the decomposition of hydrogen peroxide, and a series of filters to achieve the separation of precipitated iron compounds, and carbon filters to remove organic matter, and ultraviolet light to sanitize the water along with a second addition of hydrogen peroxide. Such process requires more equipment and is focused on the treatment of wastewater from the aseptic packaging machine (water, product, detergents, oils, etc.), unlike the proposed invention which is focused on preventing incrustations and scale inside the sterile air exchanger and elimination of residual hydrogen peroxide and recycling the wastewater from the process in the aseptic packaging machine.

Therefore, we realize that there is a need for a scale prevention system, and elimination of residual hydrogen peroxide and recycling Water used in an aseptic packaging systems of cardboard containers, preventing the formation of incrustations and scale in the sterile air heat exchanger, reducing stoppages for cleaning the air exchangers as well as saving first-use or fresh water, for this purpose the present invention has been developed, which is detailed below continuation.

SUMMARY OF THE INVENTION

The present invention is intended to be applied in air washing systems in packaging machines for laminated carton containers, to avoid unnecessary shutdown of said systems due to the maintenance of sterile air heat exchangers, to remove scale, this purpose is achieved by integrating a system that prevents the salts from precipitating and form scale in the sterile air heat exchanger, as well as eliminating the residual Hydrogen Peroxide.

The present invention in related to a system consisting of a closed loop system that has two tanks with water with the following features: conductivity of 2 micromhos and maximum silica of 0.1 ppm respectively, as well as a filtration system using activated carbon, green sand or a combination of both and an ultraviolet light lamp as a filter medium, which allows the water used to wash the air to be reused sterile, preventing salts from precipitating and embedding in the sterile air heat exchanger, as well as eliminating the residual hydrogen peroxide in aseptic packaging machines, which reduces the consumption of first-use water required for this operation, as well as increasing production by keeping the sterile air heat exchanger clean, therefore it is:

A main objective of the present invention, to provide water to the air washing system in packaging machines with the adequate requirements, that is, conductivity and maximum silica of 2 micromhos and 0.1 ppm respectively, where the dissolved solids (conductivity) present in the carry-over of water will be kept to a minimum, which will considerably reduce the presence of scale and deposits in the sterile air exchanger.

Another objective of the invention is to provide a closed loop system, where the water that washes the residual hydrogen peroxide decreases the concentration of this compound, as well as its concentration in the aseptic chamber, causing adequate concentrations of the ford in the containers and product to be sanitized.

Yet another objective is to eliminate the residual hydrogen peroxide with the use of the filtration system proposed in the present invention, allowing the water to be recirculated, reducing the consumption of first-use water, likewise the temperature will tend to increase. therefore, it is necessary to control the temperature stabilizing the normal operating conditions.

Yet another objective of the invention is to extend the operational run of the packaging machine by preventing the formation of incrustations, as well as the elimination of residual hydrogen peroxide and recirculation of water used for air washing, in aseptic packaging systems using containers. containing laminated carton. What constitutes a practical, economical and efficient alternative that manages to increase production by keeping the sterile air exchanger clean, avoiding unscheduled stoppages for cleaning.

Yet another objective of the invention is to provide a system that prevents incrustations and deposits in the sterile air exchanger and recycles the water used from the air washer (scrubber), increasing production due to stoppages for cleaning and reducing use of water of first use.

Another objective of the present invention is to solve the incrustations and deposits that occur in the sterile air exchanger, which causes pressure and temperature losses in the aseptic chamber, which puts the sterilization conditions at risk in packaging.

The characteristics of this novel Scale and Deposits Prevention System and Removal of Hydrogen Peroxide Residual and Recycling of Water Used in Aseptic container filling Systems are detailed in the following description and the drawings of the present invention.

BRIEF DESCRIPTION OF THE DRAWINGS

To complement the description that is being made and in order to help a better understanding of the features of the invention, the present drawings are attached as an integral part of the description. In which, with an illustrative and non-limiting nature are representing the following.

DETAILED DESCRIPTION OF THE INVENTION

Follows a detailed description of the present invention is given with reference to the figures.

During the aseptic packaging process of the prior art, it is frequent to stop production in order to clean/remove the incrustations and scale/deposits that are formed inside the sterile air exchanger, this due to the decrease in pressure and temperature in the aseptic chamber, which in turn puts in risk the aseptic conditions for packaging.

Figure 1:
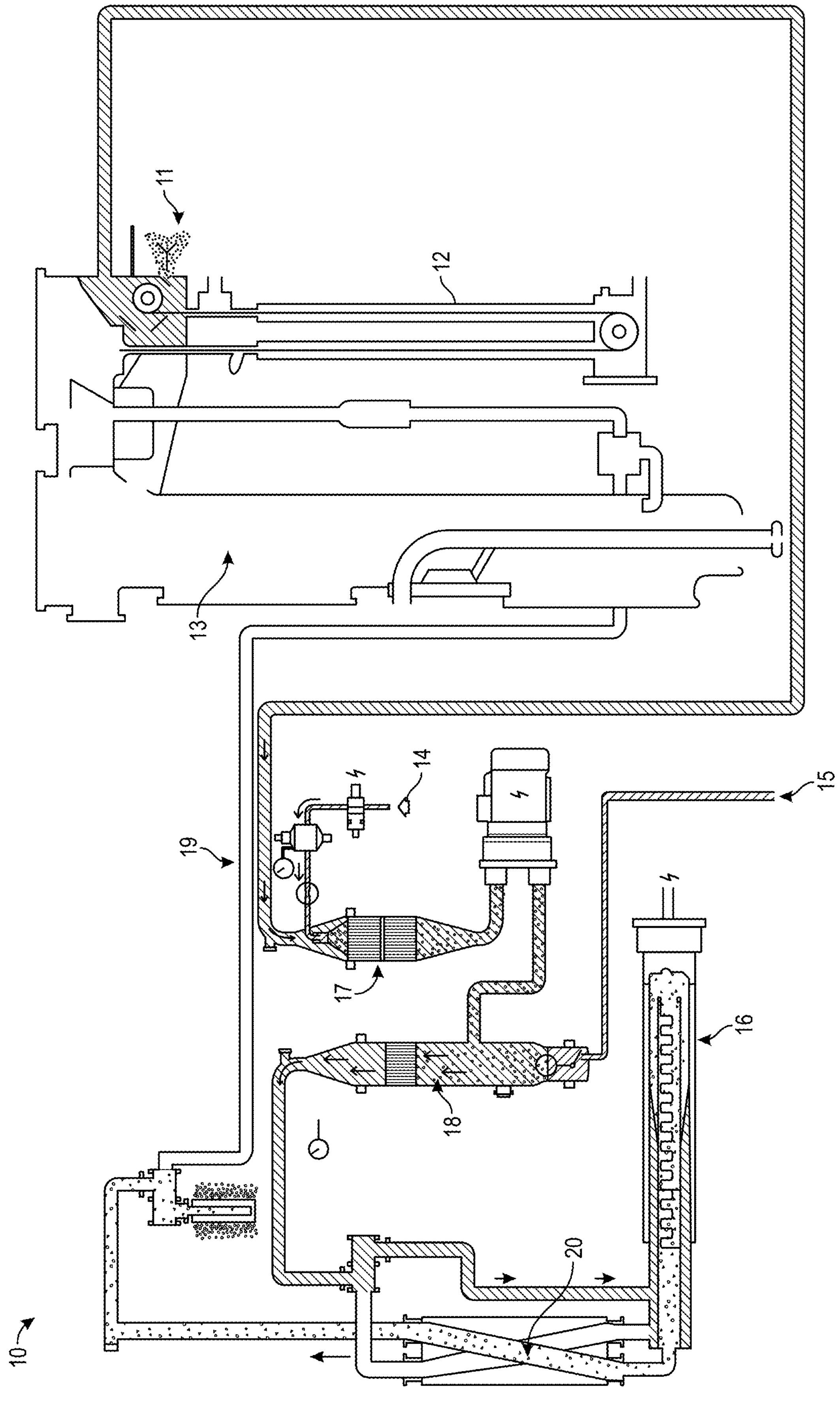
FIG. 1 shows a general diagram of the air washing system in packaging machines.
Figure 2A:
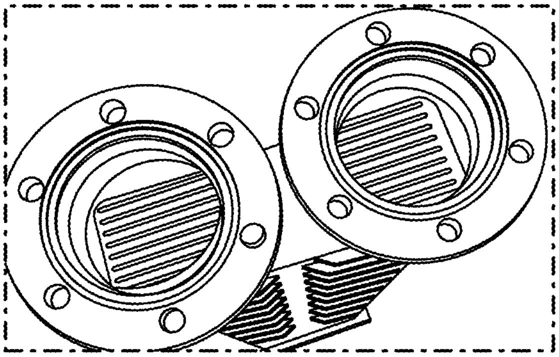
FIG. 2 shows a series of views (a, b and c) of the exchanger, with scale formation in the sterile air heat exchanger.
Figure 2B:
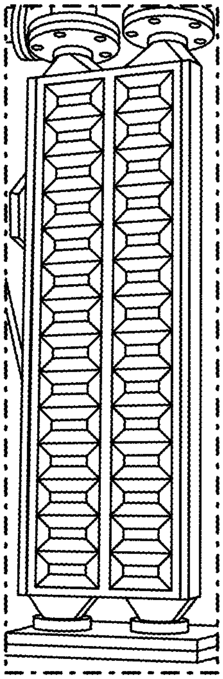
Figure 2C:
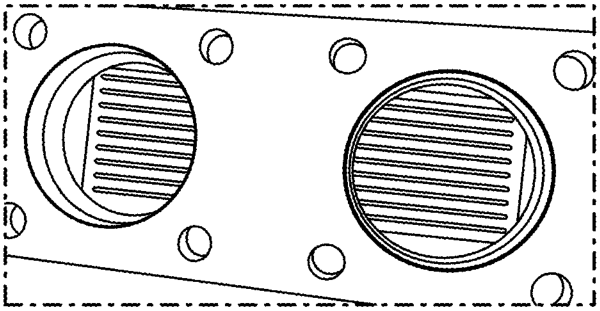

Referring to FIG. 1, it shows the washing of the air used in aseptic packaging machines of laminated carton containing containers the prior art, in said figure it is shown that the air is sent to a scrubber 17 whose purpose is to absolve the residual hydrogen peroxide present in the air, subsequently the water with hydrogen peroxide passes to an air-water separator 18.

Figure 7:
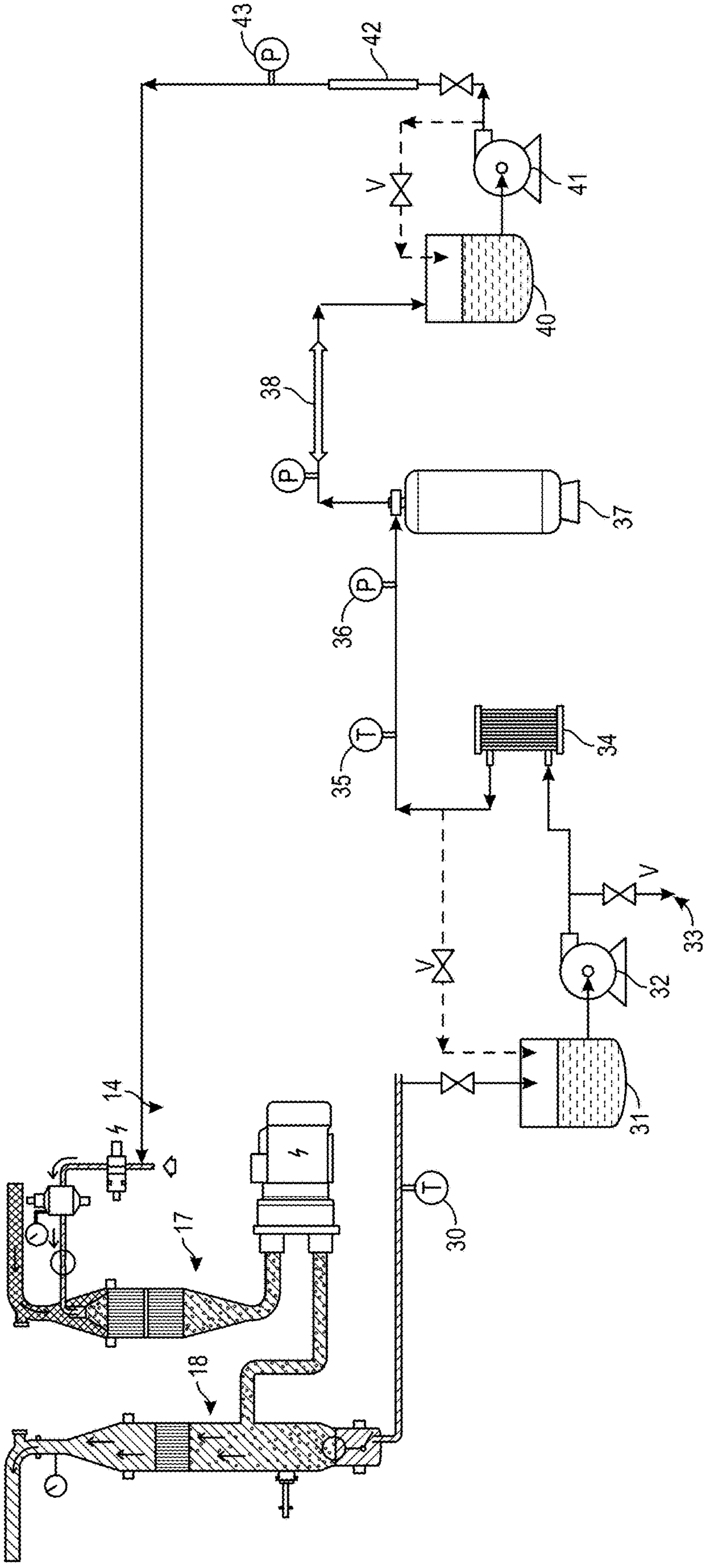
FIG. 7 shows a general diagram of the closed loop system reusing the spent water to wash again the sterile air.
Figure 8:
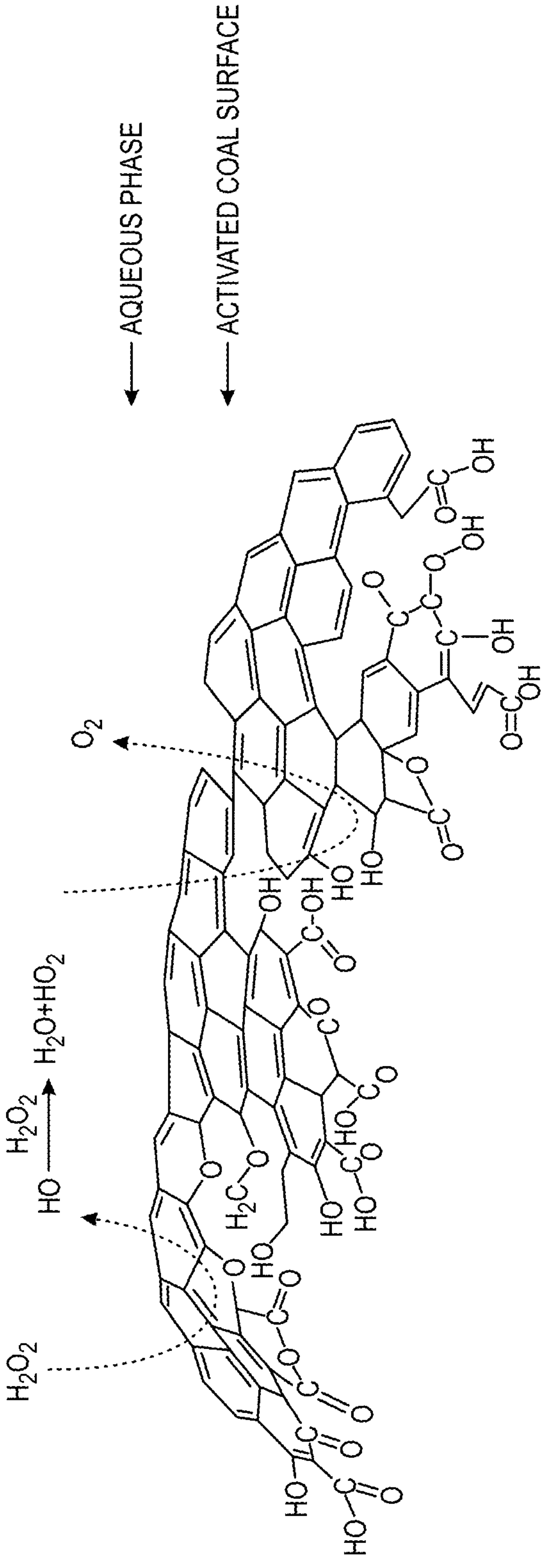
FIG. 8 shows the Image of the Hydrogen Peroxide removal mechanism in the filtration system.

According to the prior art, the water is withdrawn from the separator and sent to a drain 15, and the air is sent to the air heater 16. In accordance with the present invention, it is provided a new loop for a Residual Hydrogen Peroxide Removal System and Recirculation of Water Used in Aseptic Laminated carton Packaging Systems, shown in FIG. 7. In one aspect of the invention, the water is no longer discharged to the drain, but the water is treated to remove hydrogen peroxide and is then recycled to the aseptic packaging system of the prior art.

Said System for the Elimination of Residual Hydrogen Peroxide and Recirculation of Water Used in Aseptic Packaging Systems for containers containing Laminated carton, of the present invention, refers to the installation of a closed loop system consisting of:

1) A supply of demineralized, deionized, osmosed water, or obtained by distillation process with the following characteristics:

| | |
|---|---|
| Conductivity at 20° C. | 2.0 micromhos maximum |
| Suspended Solids | 0 ppm maximum |
| pH 20° C. | 5.0 to 7.0 |
| Silica | 0.1 ppm maximum |
| Appearance | colorless transparent liquid |
| Odor | Odorless |

Said water supply is stored in a water tank 40. From said tank 40, the water is pumped to a scrubber 17 where water absorbs hydrogen peroxide.

2) Water collection tank(s) 31, with a content of hydrogen peroxide, at the outlet of the separator 18, in case there is not enough pressure to feed the chiller 34 and filtration system 37.

3) Water chiller or heat exchanger 34, at the outlet of said collection tank(s) 31.

4) Hydrogen peroxide filtration/removal system, whose tank can be made of stainless steel or polyethylene covered with fiberglass 37 using activated carbon of vegetable or mineral origin, green sand or a mixture of both, as a filter medium, in any proportion. Where the ratio of activated carbon and green sand depends on the content of hydrogen peroxide, water flow and speed of the packaging machine.

5) Ultraviolet lamp 38 for degradation of traces of residual hydrogen peroxide.

6) Pumps 32 and 41 and accessories for connection.

According to the prior art, the salts that cause scale and deposits present in the sterile air exchanger 20 in an aseptic packaging system, come from entrainments from the water incorporated to the air stream in the air-water separator equipment 18, such entrainments pass in turn to an air heater 16 and later to a heat exchanger 20 which is required for conditioning the sterile air (at a temperature of 280° C. in start-up conditions and 70° C. in normal operating conditions) to be feed to the aseptic chamber 13 and thus ensuring the aseptic conditions required in the packaging process and avoid contamination of the product by microorganisms. Under this temperature conditions all the salts dissolved in the water will precipitate and will cause incrustations of retrograde solubility salts which highly insulate the transfer of heat, as well as the precipitation of the other salts in the form of deposits (chlorides, sulphates, sodium, Silica, etc.) due to dry conditions.

According to the prior art, the water used for air washing has the following general specifications; Total Hardness from 50 to 100 ppm as $CaCO_3$, Chlorides maximum 49 ppm as NaCl, Sulphates maximum 100 ppm as $SO_4$, Maximum Copper 0.05 ppm as Cu, pH 7.0 to 8.5 and maximum conductivity of 625 micromhos.

The water used for the washing of sterile air, (numeral 14, FIG. 1), according to the prior art usually comes from different aquifers such as well water, surface water, or treated water, maintaining a drinkable water quality for this use, using softeners to remove hardness.

For example, the analysis of sampled well water from the Ecatepec area is shown in Table 1 below:

TABLE 1

Chemical analysis of raw water and general specifications of the water at the scrubber inlet

| Property | Units | Water plant (raw) | Reference values |
|---|---|---|---|
| Total hardness | ppm as $CaCO_3$ | 300 | 50 to 100 |
| Calcium hardness | ppm as $CaCO_3$ | 110 | 20 to 40 |
| Magnesium hardness | ppm as $CaCO_3$ | 190 | 30 to 60 |
| P Alkalinity | ppm as $CaCO_3$ | 0 | |
| M Alkalinity | ppm as $CaCO_3$ | 345 | |
| Chlorides | ppm as NaCl | 332 | 49 max |
| Silica | ppm as $SiO_2$ | 86 | |
| pH | | 7.3 | 7 to 8.5 |
| Conductivity | Microohm | 866 | 625 max |
| Iron | ppm as Fe | 0.06 | |
| Sulphates | ppm as $SO_4$ | 42 | 100 max |
| Cuper | ppm as Cu | 0.1 | 0.05 max |

The first salts to form incrustations are those with retrograde solubility and low heat transfer, causing problems in heat exchange equipment, the most common incrustations found in heat exchange equipment are:

Calcium Carbonate, Calcium Sulfate, Calcium Phosphate, Silica and Magnesium Silicate.

In general, water sources have temporary hardness (in the form of Carbonates), so by eliminating the Hardness content only Silica incrustations can be formed. However, at the temperature conditions of 280° C. will take place the precipitation of others salts, mainly Sodium Chloride, Sodium Carbonate, Sodium Sulphate, coprecipitating Silica, at the temperature conditions will precipitate and will get dirty the heat exchange equipment.

Considering the reference values for Total Hardness from 50 to 100 ppm as $CaCO_3$ and simulating the compounds that precipitate using the WaterCycleRx® software from FRENCH CREEK SOFTWARE, INC., the following has been found:

There will be precipitation of Calcium Carbonate in the form of Calcite and Aragonite, these compounds precipitate from a pH of 7.5 and 86° C. considering a Total Hardness of 50 ppm, and from a pH of 7.5 and 64° C. considering a Total Hardness of 100 ppm.

Figure 3A:
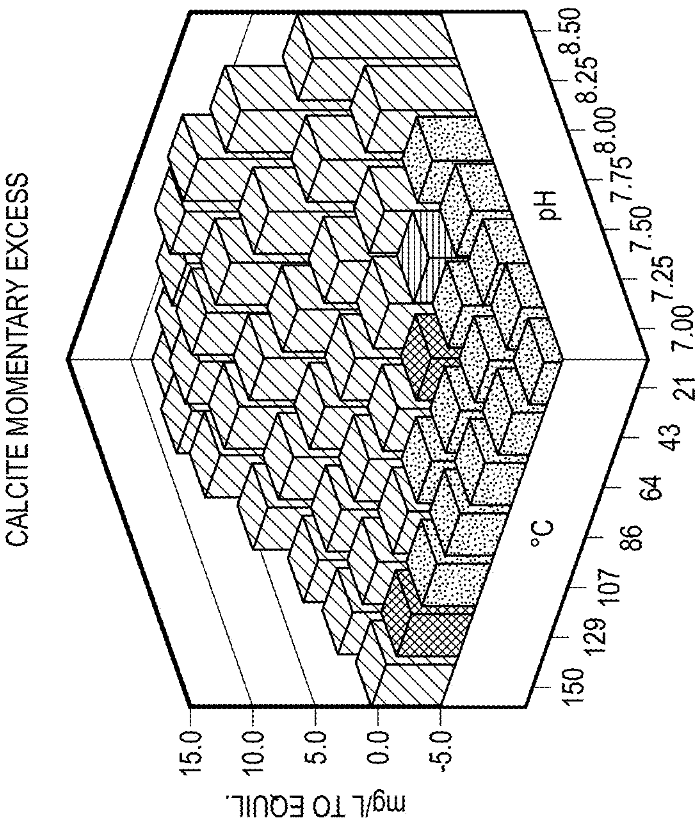
FIG. 3 shows two graphs of precipitation (a and b) of Calcium Carbonate compounds (Calcite and Aragonite) using mineral solubility simulation considering 50 ppm of total hardness in the water, present in the scrubber, as a function of pH and temperature.
Figure 3B:
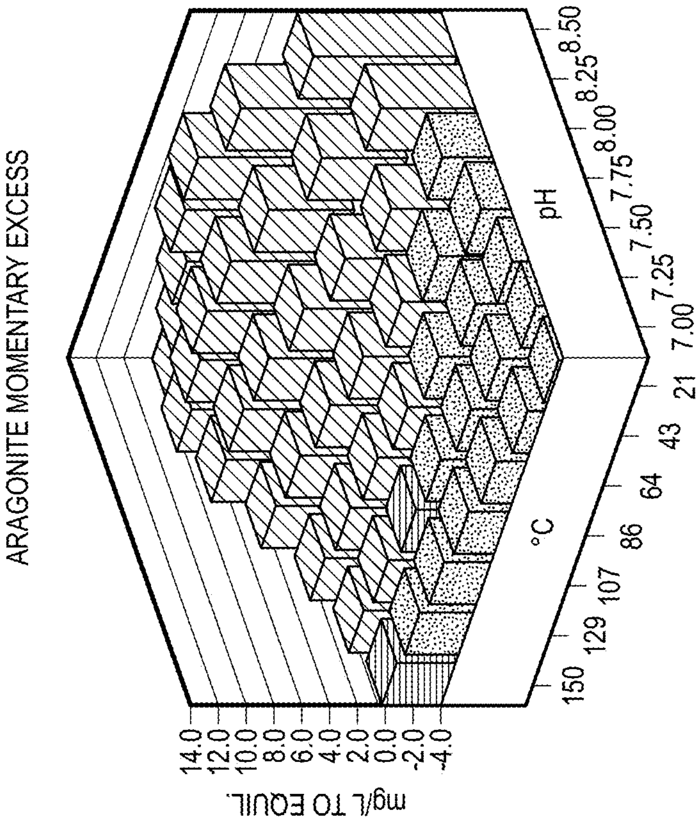
Figure 4A:
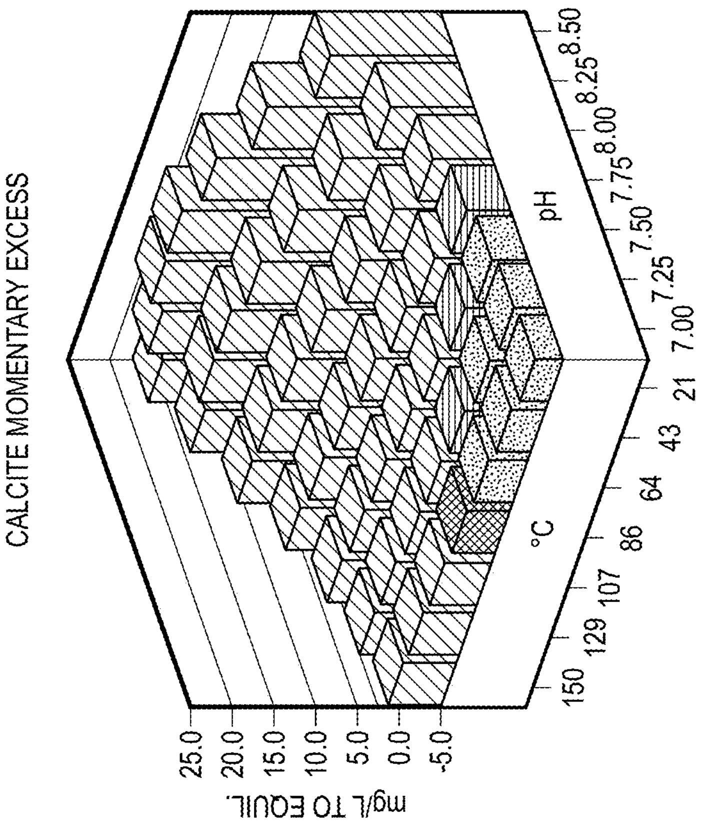
FIG. 4 shows two Graphs of precipitation (a and b) of compounds of Calcium Carbonate (Calcite and Argonite) using mineral solubility simulation considering 100 ppm of Total Hardness in the Scrubber water as a function of pH and temperature.
Figure 4B:
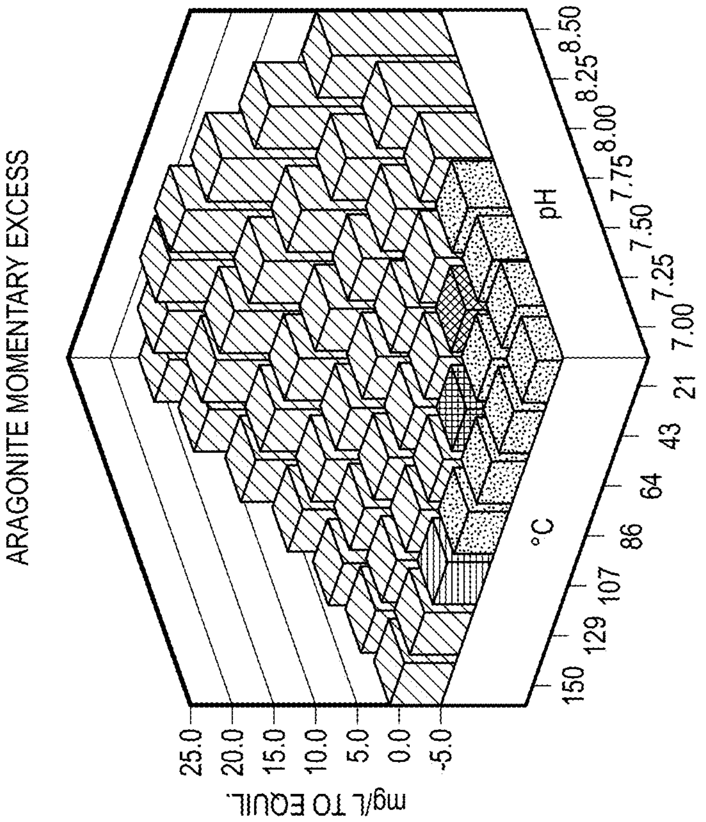
Figure 5:
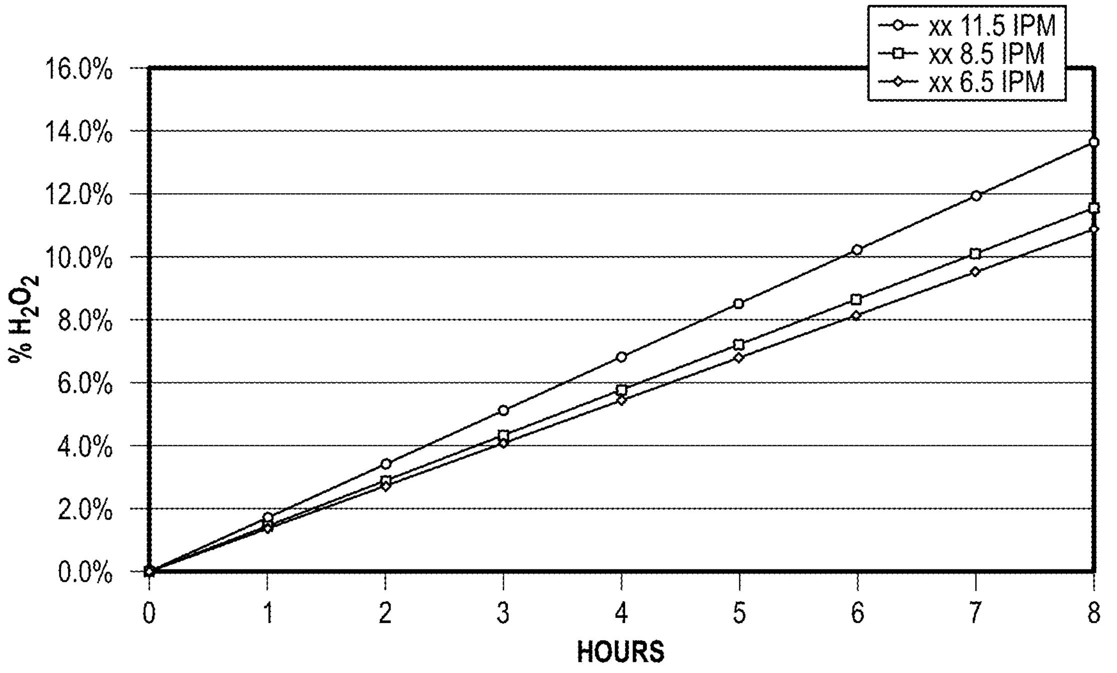
FIG. 5 shows the Hydrogen Peroxide concentration graph in the closed loop system, at the laboratory level.
Figure 6:
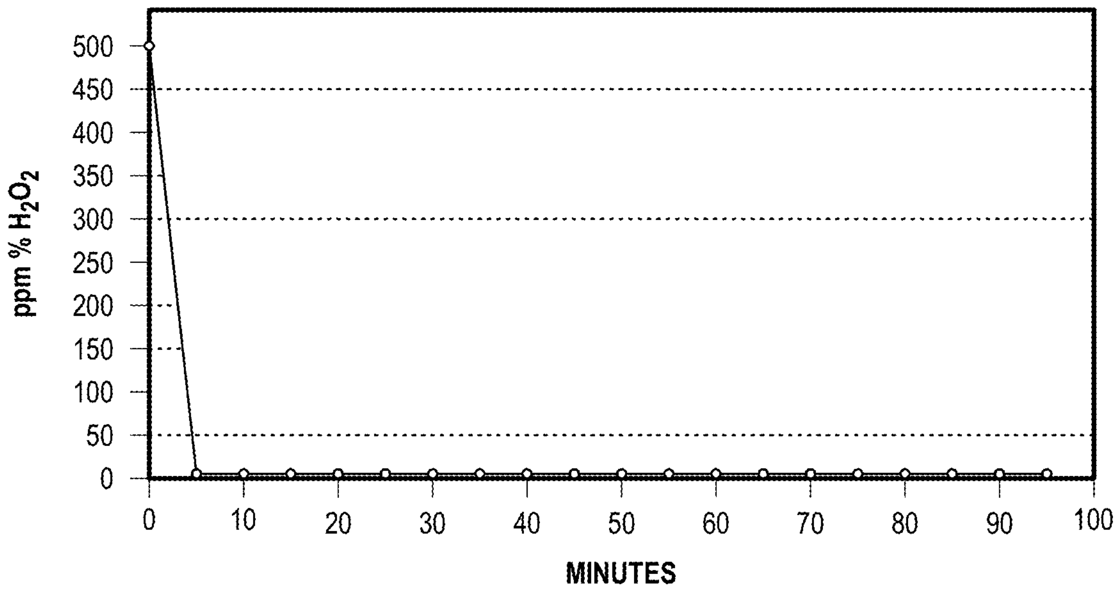
FIG. 6 shows the Hydrogen Peroxide removal graph downstream a carbon and green sand filter, at the laboratory level.

This can be seen in graph a and b of FIG. 3, regarding a simulation of mineral solubility at 50 ppm of total hardness in water entering to the Scrubber, where the color code identifies the severity of the problem, showing the following indications according to the color plotted;

Color code identifying the severity of the problem.

Blue color means a safe range.

Green means a slight potential problem if the condition changes slightly.

Yellow color warns check measurement; a problem is near.

Magenta color indicates a probable problem, take corrective action.

Red color indicates a problem. Treatment or corrective action is required.

In graph 4a and 4b mineral solubility simulation 100 ppm of total hardness in the water entering the Scrubber, where the color code identifies the severity of the problem, showing the following indications according to the color plotted;

Color code identifying the severity of the problem.

Blue color means a safe range.

Green means a slight potential problem if the condition changes slightly.

Yellow color warns check measurement; a problem is near.

Magenta color indicates a probable problem, take corrective action.

Red color indicates a problem. Treatment or corrective action is required.

From the above, it can be deduced that any trace of hardness in the water used for the sterile air washing and this is dragged into the sterile air separator, will form calcium carbonate incrustations and the other salts will precipitate due to the effect of temperature.

In accordance with the present invention, to prevent the formation of encrustations, demineralized, deionized, osmosed water is used, or else obtained by the distillation process (distilled water, bidistilled water, tri-distilled water) for washing sterile air with the following characteristics:

| | |
|---|---|
| Conductivity at 20° C. | 2.0 micromhos maximum |
| Silica | 0.1 ppm maximum |
| In addition, the water may have Suspended Solids | 0 ppm maximum |
| pH 20° C. | 5.0 to 7.0 |

The content of dissolved salts is minimal since the conductivity is an indirect form of the dissolved salts in the water, therefore, although these are entrained in the sterile air separator, the amount of deposit/scale that will be formed in the Sterile air heat exchanger will be minimal. Which results in minimizing stoppages for cleaning, thereby increasing the production of the aseptic packaging machine.

According to the prior art, the consumption of water for sterile air washing varies depending on the container, as well as the characteristics and speed of each packaging machine, the average flow being from 5.0 to 22 liter/min, this water is discarded (numeral 15, FIG. 1) due to the residues of Hydrogen Peroxide resulting from the sterile air washing, being a high water consumption and cost if the number of packaging machines in operation are considered.

If the drain water 15 from the prior art were to be reused without any treatment, the residual Hydrogen Peroxide would increase from 0 ppm to 11,500 ppm (equivalent to 11.5%) of residual Hydrogen Peroxide in 8 hours with At a flow of 8.5 liters/min, the reference value is a maximum of 1% residual Hydrogen Peroxide in the water at the outlet of the sterile air separator, such high concentrations of hydrogen peroxide would cause contamination of the aseptic chamber as well as contamination of the containers produced and food contained.

According to the present invention, to recycle this water, the present invention removes the residual Hydrogen Peroxide. For this purpose, the following stages are carried out: (1) a stage of contact with activated carbon, green sand or a mixture of both in any proportion, and (2) a stage of contact with ultraviolet light.

For the stage of contact with activated carbon, green sand or mixtures of both in any proportion, it is required a filtration equipment whose tank can be made of stainless steel or polyethylene covered with fiberglass 37 where the Hydrogen Peroxide molecule is broken into Oxygen and Water without adding an additional contaminant to the aseptic system.

Filtration equipment 37 contains vegetable or mineral type activated carbon, green sand (commercially available) or a combination of both in any proportion.

The mechanism for the removal of peroxide in the filtration system 37 with activated carbon and green sand is as follows:

$$AC + H_2O_2 \longrightarrow AC^+ + OH^- + OH^\circ$$

$$AC^+ \longrightarrow AC + H^+ + OOH^\circ$$

Activated carbon (AC) has reducing characteristics so hydrogen peroxide will not be absorbed on it.

The radicals OOH° and OH° combine to form $H_2O$ and $O_2$.

In the Green Arena, the reactions that take place are:

$$2H_2O_2 + MnO_2 \longrightarrow 2\,H_2O + O_2$$

The contact time for the elimination of the residual Hydrogen Peroxide varies from 5 minutes to 30 minutes and will depend on the concentration of Peroxide to be removed, as well as the flow that passes through the filter 37 adjusting the filter media bed.

Example 1: Water with a hydrogen peroxide content of 500 ppm was passed through a column containing activated carbon and green sand during a 95 minute run at the laboratory level. As a result, it was obtained the reduction of the residual Hydrogen Peroxide from 500 ppm to 4 ppm.

Example 2: In an operational run in a packaging machine, the hydrogen peroxide content was decreased from 250 ppm to 0.02 ppm.

Since an increase in the temperature of the water in the closed loop system takes place due to contact with the hot air and other areas of the packaging machine, according to the present invention it is installed a water cooling system, for example: a chiller, a heat exchanger 34 such as a plate heat exchanger, tube and shell heat exchanger or air heat exchanger to maintain the temperature at a suitable value for the operation of the machine, for example, between 15 and 25° C. The system of the present invention includes a bypass when cooling is not required, since the temperature of the water without cooling reaches values of 61° C. at the outlet of the scrubber 17.

According to the present invention, for the elimination of traces of Hydrogen Peroxide, as well as ensuring sterile water, at least one ultraviolet light lamp 38 is optionally placed to carry out a process of decomposing the traces of hydrogen peroxide through an advanced oxidation process.

The advanced oxidation process using Hydrogen Peroxide and ultraviolet light gives rise to the formation of hydroxyl radicals which are highly reactive, they attack and decompose organic matter and disinfect the water.

The advanced oxidation mechanism for the decomposition of Hydrogen Peroxide is the following:

$$H_2O_2 \xrightarrow[HV<380\ nm]{} 2OH^\circ$$

$$OH^\circ + H_2O_2 \xrightarrow[HV]{} OH_2^\circ + H_2O$$

$$OH_2^\circ + H_2O_2 \xrightarrow[HV]{} OH^\circ + H_2O + O_2$$

In accordance with the present invention, the system for preventing scale and deposits in the sterile air heat exchanger 20 as well as for the elimination of residual hydrogen peroxide and recirculation of water used for air washing, in systems of Aseptic packaging 10 using laminated carton-containing containers constitutes a practical, economical and efficient alternative, increasing production by keeping the sterile air exchanger clean, avoiding unscheduled stoppages for cleaning and saving water for the first use.

In another aspect of the invention there is provided a method for modernizing an existing food packaging plant. The method comprises the steps of:

a. install a sterile air wash water supply tank that exhibits the following properties:

| | |
|---|---|
| Conductivity at 20° C. | 2.0 micromhos maximum |
| Silica | 0.1 ppm maximum; |

b. installing a sterile air wash water supply line to a scrubber 17, to wash sterile air;

c. installing a collection tank 31, to collect washing water with the presence of hydrogen peroxide at the outlet of an air-water separator 18 coming from the scrubber 17, of an air washing system 10;

d. installing a line and means to transfer the water from tank 31 to a chiller or heat exchanger 34;

e. installing a chiller or heat exchanger 34, at the outlet of the collection tank 31, to maintain the water temperature at a suitable value for the operation of the packaging machine;

f. install a filter medium activated carbon, green sand or mixtures thereof, in any proportion, at the outlet of the chiller or heat exchanger 34, for the elimination of hydrogen peroxide; and g. Install a sterile air wash water supply tank 40.

The sterile water cooler 34 is of the chiller type, plate heat exchanger, tube and shell heat exchanger or air heat exchanger.

In addition, the activated carbon in the filter medium is selected from activated vegetable or mineral carbon.

Optionally, between the filter media and the supply tank 40, an ultraviolet lamp 38 is installed, for the removal of traces of hydrogen peroxide by an advanced oxidation process and sterilization of the sterile air wash water.

The invention claimed is:

1. An aseptic packaging system for laminated carton-containing containers adapted to remove residual hydrogen peroxide and to recycle sterile air washing water, comprising:

a supply line to supply sterile air washing water having the following properties, a maximum conductivity at 20° C. of 2.0 micromhos, and a maximum silica content of 0.1 ppm;

a scrubber for washing the sterile air, the scrubber configured to be fed with the sterile air washing water;

an air-water separator to separate washing water coming from the scrubber, the separated water having a content of hydrogen peroxide;

a collection tank for collecting the washing water having said content of hydrogen peroxide, at the outlet from the air-water separator;

a chiller or heat exchanger, to maintain the water temperature at a suitable value for the operation of the packaging system, the chiller or heat exchanger being configured to receive water from the collection tank;

a filter comprising as a filer medium activated carbon, green sand or mixtures thereof in any ratio for the removal of hydrogen peroxide, wherein the filter is configured to receive water from the chiller or heat exchanger;

a tank for obtaining and collecting the fresh sterile air washing water; and a hydrogen peroxide water discharge line connected to the air-water separator and to the collection tank;

wherein the supply line is from the tank to the scrubber for providing the sterile air washing water.

2. The system of claim 1 wherein the activated carbon is selected from activated vegetable or mineral carbon.

3. The system of claim 1 further comprising an ultraviolet light lamp connected downstream the filter for the removal of traces of hydrogen peroxide by an advanced oxidation process and sterilization of the sterile air washing water.

4. A process of removal of residual hydrogen peroxide and recycling sterile air washing water used in an aseptic packaging system for laminated carton-containing containers, wherein the process is a closed loop system comprising:

a. providing a fresh sterile air washing water supply that exhibits the following properties:

a maximum conductivity at 20° C. of 2.0 micromhos, and a maximum content of silica of 0.1 ppm;

b. feeding the sterile air washing water to a scrubber, for washing the sterile air;

c. collecting washing water having a content of hydrogen peroxide in a collection tank, at the outlet from an air-water separator coming from the scrubber of the air washing system;

d. transferring said water to a chiller or heat exchanger, to maintain the water temperature at a suitable value for the operation of the packaging machine;

e. contacting the water coming from the chiller or heat exchanger with a filter medium comprising activated carbon, green sand or mixtures thereof in any ratio for the removal of hydrogen peroxide; and f. obtaining and collecting the fresh sterile air washing water in tank.

5. The process of removal of residual hydrogen peroxide and recycling of sterile air washing water used in the aseptic packaging system for laminated carton-containing containers according to claim 4, wherein the water used in the closed loop system is selected from demineralized water, deionized water, osmosed water, water obtained by distillation processes including distilled water, bi-distilled water, tri-distilled water.

6. The removal of residual elimination of hydrogen peroxide and recycling of sterile air washing water used in the aseptic packaging system for laminated carton-containing containers according to claim 4, wherein the water has the following properties:

a content of suspended solids of 0 ppm; and a pH at 20° C. from 5.0 to 7.0.

7. The process of removal of residual hydrogen peroxide and recycling of sterile air washing water used in the aseptic packaging system for laminated carton-containing containers according to claim 4, wherein the heat exchanger is a plates heat exchanger, tube and shell heat exchanger or air heat exchanger.

8. The process of removal of residual hydrogen peroxide and recycling of sterile air washing water used in the aseptic packaging system for laminated carton-containing containers according to claim 4, further comprising passing the washing water through an ultraviolet light lamp, for the removal of traces of hydrogen peroxide through an advanced oxidation process and sterilization of the sterile air washing water.

* * * * *